United States Patent [19]

Tsuneki et al.

[11] Patent Number: 4,558,028
[45] Date of Patent: Dec. 10, 1985

[54] CATALYST FOR PRODUCTION OF METHACRYLIC ACID

[75] Inventors: Hideaki Tsuneki, Osaka; Michio Ueshima, Nishinomiya; Ryuji Aoki, Himeji; Isao Nagai, Suita, all of Japan

[73] Assignee: Nippon Shokubai Kagaku Kogyo Co., Ltd., Osaka, Japan

[21] Appl. No.: 562,007

[22] Filed: Dec. 16, 1983

[30] Foreign Application Priority Data

Dec. 22, 1982 [JP] Japan ................................ 57-223954

[51] Int. Cl.$^4$ ........................ B01J 27/14; C07C 51/16
[52] U.S. Cl. .................................... 502/211; 502/209; 502/210; 502/212; 502/527; 562/545; 562/546; 562/547
[58] Field of Search ............... 502/209, 210, 211, 212, 502/527

[56] References Cited

U.S. PATENT DOCUMENTS

| | | | |
|---|---|---|---|
| 2,408,164 | 9/1946 | Foster | 502/527 X |
| 3,674,680 | 7/1972 | Hoekstra et al. | 502/527 X |
| 3,741,910 | 6/1973 | Shiraishi et al. | 502/212 X |
| 3,951,861 | 4/1976 | Shiraishi et al. | 502/212 X |
| 3,954,856 | 5/1976 | Kobayashi et al. | 502/212 X |
| 3,956,181 | 5/1976 | Groselli et al. | 502/212 |
| 4,075,244 | 2/1978 | Okiyama et al. | 502/209 X |
| 4,118,419 | 10/1978 | Ishii et al. | 502/212 X |
| 4,155,938 | 5/1979 | Yamamoto et al. | 502/212 X |
| 4,178,464 | 12/1979 | Sakamoto et al. | 502/209 X |
| 4,225,466 | 9/1980 | Wada et al. | 502/209 |
| 4,280,928 | 7/1981 | Kirch et al. | 502/212 X |
| 4,282,116 | 8/1981 | Reuter et al. | 502/527 X |
| 4,314,075 | 2/1982 | Shaw et al. | 502/209 X |
| 4,409,128 | 10/1983 | Krofetz et al. | 502/211 |
| 4,419,270 | 12/1983 | Ueshima et al. | 502/209 |
| 4,438,217 | 3/1984 | Tokota et al. | 502/243 X |

FOREIGN PATENT DOCUMENTS 0045853 2/1982 European Pat. Off. ............ 502/209

Primary Examiner—D. E. Gantz
Assistant Examiner—William G. Wright
Attorney, Agent, or Firm—Sherman & Shalloway

[57] ABSTRACT

A catalyst for production of methacrylic acid, said catalyst being molded in a ring-like shape having an outside diameter of 3.0 to 10.0 mm, an inside diameter 0.1 to 0.7 times the outside diameter and a length 0.5 to 2.0 times the outside diameter, said catalyst comprising a catalytically active material having the composition represented by the following general formula

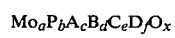

$$Mo_aP_bA_cB_dC_eD_fO_x$$

wherein Mo is molybdenum, P is phosphorus, A is at least one element selected from the group consisting of arsenic, antimony, germanium, bismuth, zirconium and selenium, B is at least one element selected from the group consisting of copper, iron, chromium, nickel, manganese, cobalt, tin, silver, zinc and rhodium, C is at least one element selected from the group consisting of vanadium, tungsten and niobium, D is at least one element selected from the group consisting of alkali metals, alkaline earth metals and thallium, and O is oxygen, and a, b, c, d, e, f and x represents the atomic ratios of Mo, P, A, B, C, D and O provided that when a is 12, b is 0.5 to 4, c is 0 to 5, d is 0 to 3, e is 0 to 4 and f is 0.01 to 4 and x is a number determined by the oxidation states of the individual elements.

3 Claims, No Drawings

CATALYST FOR PRODUCTION OF METHACRYLIC ACID

This invention relates to a catalyst for obtaining methacrylic acid in a high selectivity and a high yield by catalytic vapor-phase oxidation or oxidative dehydrogenation of methacrolein, isobutyraldehyde or isobutyric acid with air or a gas containing molecular oxygen.

Many catalysts have already been proposed for the production of methacrylic acid from methacrolein, isobutyraldehyde or isobutyric acid. They include, for example, the catalysts disclosed in the specifications of U.S. Pat. Nos. 4075244, 4225466 and 4118419, European Pat. No. 6,248 and French Pat. No. 2,442,825. However, when these known catalysts are actually used in industrial practice, it is difficult to give such high selectivities and yields of methacrylic acid as described in the working examples of these patent documents, and the results obtained are frequently on far lower levels. There are probable causes. For example, since in an actual industrial process, catalytic vapor-phase oxidation is very exothermic and high temperatures are created in the inside of catalyst particles of a practical size, the oxidation reaction proceeds to an excessive extent. Or because the height of the catalyst layer is large, the pressure incessantly varies in the catalyst layer from the gas inlet toward the gas outlet of the reactor, and the reaction is far from an ideal one.

The present inventors have worked on the development of a catalyst free from these inconveniences, namely a catalyst which can give methacrylic acid in a high yield while enabling a reaction to be carried out at a high space velocity in an industrial process, and consequently found that a ring-shaped catalyst having a specific size gives much better results than conventional spherical or solid cylindrical catalysts.

Thus, according to this invention, there is provided a catalyst for production of methacrylic acid, said catalyst being molded in a ring-like shape having an outside diameter of 3.0 to 10.0 mm, preferably 4.0 to 8.0 mm, an inside diameter 0.1 to 0.7 times, preferably 0.2 to 0.6 times, the outside diameter and a length (or height) 0.5 to 2.0 times, preferably 0.7 to 1.3 (or height) 0.5 to 2.0 times, preferably 0.7 to 1.3 times, the outside diameter, said catalyst comprising a catalytically active material having the composition of the following general formula

$$Mo_aP_bA_cB_dC_eD_fO_x$$

wherein Mo is molybdenum, P is phosphorus, A is at least one element selected from the group consisting of arsenic, antimony, germanium, bismuth, zirconium and selenium, B is at least one element selected from the group consisting of copper, iron, chromium, nickel, manganese, cobalt, tin, silver, zinc and rhodium, C is at least one element selected from the group consisting of vanadium, tungsten and niobium, D is at least one element selected from the group consisting of alkali metals, alkaline earth metals and thallium, and O is oxygen; and a, b, c, d, e, f and x represent the atomic ratios of Mo, P, A, B, C, D and O respectively provided that when a is 12, b is 0.5 to 4, c is 0 to 5, d is 0 to 3, e is 0 to 4 and f is 0.01 to 4, and x is a number determined by the oxidation states of the individual elements.

The ring-like shape of the catalyst of this invention may be described as a cylinder having an outside diameter of 3.0 to 10.0 mm, preferably 4.0 to 8.0 mm, and a length 0.5 to 2.0 times, preferably 0.7 to 1.3 times, the outside diameter with a through hole having a diameter 0.1 to 0.7 times, preferably 0.2 to 0.6 times, the outside diameter being provided centrally and vertically of the cylinder.

The catalyst of this invention has the following four excellent performances which are more specifically disclosed in Examples given hereinbelow.

(I) Because of the ring-like shape of the above-specified size, the geometric surface area of the catalyst increases and the length of pores of the catalyst is shortened. As a result, methacrylic acid formed in the catalyst pores can be more rapidly removed than in the case of cylindrical catalysts, and a reaction of methacrylic acid to acetic acid, carbon dioxide and carbon monoxide, which is an undesired consecutive reaction, is reduced.

(II) Since the catalyst has a ring-like shape of the above-specified size, voids increase and the pressure drop in the catalyst layer decreases. Consequently, the cost of power consumption by a blower in industrial production can be curtailed. It is seen from Example 6 and Comparative Example 4 given hereinafter that the pressure drop in a layer of a solid cylindrical catalyst having an outside diameter of 6.0 mm and a length of 6.6 mm is on the same level as the pressure drop in a layer of a ring-shaped catalyst having an outside diameter of 5.0 mm, a length of 5.5 mm and a through-hole diameter of 2.0 mm. Accordingly, in the present invention, the catalyst is more particulate and has an increased geometrical surface area, and a higher activity and a higher yield can be obtained correspondingly.

(III) The catalyst of this invention is especially advantageously used for the production of methacrylic acid from a methacrolein-containing gas obtained by the catalytic vapor-phase oxidation of isobutylene or tertiary butanol. More specifically, for the industrial production of methacrylic acid by the oxidation of isobutylene or tertiary butanol, there are available (1) a "first-second stage separated process" which comprises catalytically oxidizing isobutylene or tertiary butanol in the vapor phase with molecular oxygen in the presence of an oxide catalyst comprising molybdenum, cobalt, bismuth and iron to form methacrolein as a main product (a first-stage reaction), trapping and separating methacrolein in the product gas of the first-stage reaction, mixing it with air, steam, an inert gas, etc., and introducing the mixture into a second-stage reactor packed with a molybdenum-phosphorus-containing heteropolyacid catalyst, thereby forming methacrylic acid, and (2) a "first-second stage connected process" in which the product gas of the first-stage reaction is directly used as a starting gas in the second-stage reaction. In the first-second stage separated process, methacrolein is trapped and separated from the first-stage reaction gas, and a starting gaseous mixture for the second-stage reaction is newly prepared. Hence, it requires much utility and equipment, and is economically disadvantageous as compared with the first-second stage connected process. The first-second stage connected process, however, is not without disadvantage. The product gas of the first-stage reaction contains considerable amounts of high-boiling by-products composed mainly of terephthalic acid and a tarry material in addition to low-boiling by-products such as acetaldehyde, acrolein, acetone and acetic acid. The high-boiling by-products are composed of dimers or polymers of isobutylene, methacrolein, methacrylic acid, etc. Their kinds and amounts increase especially when an oxide catalyst comprising molybdenum, cobalt, bismuth and iron is used in the first-stage reaction. Accumulation of these high-boiling by-products on the second-stage catalyst causes an increase in the pressure drop of the catalyst layer, and may simultaneously result in a reduction in catalytic activity and selectivity. The catalyst of this invention exhibits a marked effect when used in such a first-second stage connected process, and can markedly reduce the increase of the pressure drop of the catalyst layer and the disadvantage of the reduced catalyst performance, which are due to the accumulation of the high-boiling by-products.

(IV) The catalyst of this invention has the advantage of possessing an increased life. Methacrylic acid which is the main product of the second-stage reaction and is also formed in a small amount in the first-stage reaction and introduced into the second-stage reaction is thermally more unstable than other carboxylic acids, for example acrylic acid, produced by an oxidation reaction of the same type. This tendency is increased especially as the temperature of the catalyst layer becomes higher. When the ring-shaped catalyst of this invention is applied to such a reaction, its good heat-removing effect make it possible to inhibit accumulation of the heat of reaction on the catalyst layer, i.e. the occurrence of localized high-temperature portions, and to prevent the increasing of the aforesaid decomposition reaction of methacrylic acid to acetic acid, carbon dioxide and carbon monoxide. By the dual effect of the reduced heat generation and the good heat-removing ability, the temperature of the high-temperature portion of the catalyst layer is maintained at a low value, and a heteropolyacid and its salt, which are the active ingredients, do not easily undergo thermal structural destruction during the reaction. Consequently, the life of the catalyst is prolonged.

The catalyst of this invention can be prepared by a known method. As will be clear from Examples and Comparative Examples shown hereinbelow, the effects of the present invention are clearly observed irrespective of the methods of catalyst preparation. For example, the catalyst of the invention can be prepared by adding, as required, a molding aid such as carbon black, stearic acid, starch, polyacrylic acid, a mineral oil or a vegetable oil, a reinforcing agent such as inorganic fibers (e.g., glass fibers, asbestos fibers, etc.), or an inorganic fine powder (e.g., a metal powder, or metal flakes), and water to a starting mixture in the form of a powder or clay obtained by a precipitation method, a kneading method, etc., molding the mixture into a ring-like shape by a tabletting machine, an extruder, etc., and calcining the molded material at a temperature of 150° to 500° C. in the air or in a stream of an inert gas such as nitrogen.

One example of a preferred method of preparing the catalyst of the invention is shown below. A molybdenum compound such as ammonium paramolybdata and a vanadium compound such as ammonium metavanadata are dissolved or dispersed in water, and a nitrogen-containing heterocyclic compound such as pyridine and phosphoric acid are added. Then, an aqueous solution of an alkali metal nitrite is added. As required, compounds of components A and B are added. The mixture is concentrated by heating, and a molding aid or a reinforcing agent is added to the resulting clay-like material. It is then extruded, dried and calcined first in a nitrogen stream and then in the air to obtain a finished catalyst.

Compounds which can be decomposed to oxides in the catalyst preparing step described above are recommendable as the raw materials used for the preparation of the catalyst of this invention. They include, for example, nitrates, ammonium salts, organic acid salts, hydroxides, oxides, metal acids, and ammonium salts of metal acids. The alkali metal is selected preferably from potassium, rubidium and cesium. Examples of the alkaline earth metal are magnesium, calcium, strontium and barium, the last one being especially preferred.

A catalytic oxide having the composition represented by the above general formula would not be able to achieve the desired performance in industrial use if its shape is not a ring-like shape having the above-specified size. This can be seen from Comparative Examples given hereinbelow. The ring-like catalyst of this invention exhibits a very good catalytic performance when its thickness (i.e., one-half of the difference between the outside diameter and the inside diameter) is 0.1 to 4.0 mm on an average. If the thickness is too small, the strength of the catalyst will be reduced. Preferably, therefore, it is at least 1.0 mm.

The catalytic vapor-phase oxidation or oxidative dehydrogenation reaction in accordance with this invention is carried out by introducing a gaseous starting mixture composed of, for example, 1.0 to 10% by volume of a starting compound such as methacrolein, isobutyraldehyde or isobutyric acid, 1 to 10 parts by volume, per part by volume of the starting compound, of molecular oxygen, and an inert gas as a diluent such as nitrogen, carbon dioxide gas or steam (the use of steam is particularly advantageous because it inhibits formation of by-products and increases the yield of the desired final product) into the catalyst prepared as above at a space velocity (STP) of 100 to 5000 $hr^{-1}$, a temperature of 200° to 400° C., and a pressure from atmospheric pressure to 10 atmospheres. When methacrolein is selected as the starting compound, it needs not to be entirely pure, and may be a methacrolein-containing gas obtained by catalytically reacting isobutylene or tertiary butanol in the manner described hereinabove. In an industrial process, the latter is particularly recommended.

The following Examples and Comparative Examples illustrate the present invention in greater detail. It should be understood however that the invention is not limited to these examples.

The conversion, selectivity and one-pass yield as used in the present application are defined as follows:

$$\text{Conversion (\%)} = \frac{\text{Moles of the starting compound reacted}}{\text{Moles of the starting compound fed}} \times 100$$

$$\text{Selectivity (\%)} = \frac{\text{Moles of methacrylic acid formed}}{\text{Moles of the starting compound reacted}} \times 100$$

$$\text{One-pass yield (\%)} = \frac{\text{Moles of methacrylic acid formed}}{\text{Moles of the starting compound fed}} \times 100$$

EXAMPLE 1

Ammonium paramolybdate (1766 g) and 106 g of ammonium metavanadate were dissolved with stirring in 8000 ml of heated water. Pyridine (406 g) and 104.8 g of phosphoric acid (85% by weight) were added to the solution, and thereafter, 800 ml of nitric acid (specific gravity 1.38; all nitric acids described hereinafter have the same specific gravity) was added. Furthermore, a solution of 162.4 g of cesium nitrate in 1000 ml of water was added, and with stirring, the mixture was concentrated by heating. The resulting slurry-like material was dried at 250° C. for 15 hours, and then pulverized. Water was then added as a molding aid, and the mixture was molded into a ring-like shape having an outside diameter of 6.0 mm, a length of 6.6 mm and an inside diameter (a through-hole diameter) of 1.0 mm. The molded product was dried and calcined in a nitrogen stream at 430° C. for 3 hours and then in air at 400° C. for 3 hours. The resulting catalytic oxide had the following composition in atomic ratio (excepting oxygen; the same applies hereinafter).

$$Mo_{12}P_{1.09}V_{1.09}Cs_{1.0}$$

1500 ml of the resulting catalyst was filled in a steel reaction tube having a diameter of 25.4 mm in a layer length of 2960 mm. A gaseous mixture obtained by catalytic vapor-phase oxidation of isobutylene in the presence of an oxide catalyst comprising molybdenum, cobalt, tungsten, bismuth and iron (prepared in accordance with Example 21 of U.S. Pat. No. 3,825,600) was introduced into the catalyst layer, and reacted at a temperature of 290° C. and a space velocity of 1200 hr$^{-1}$. The pressure drop during the reaction and the yield of the product are shown in Table 1.

The gaseous mixture had the following average composition.

|  |  |
|---|---|
| Methacrolein | 3.5% by volume |
| iso-Butylene | 0.04 by volume |
| Methacrylic acid and acetic acid | 0.24 by volume |
| Steam | 20 by volume |
| Oxygen | 9.0 by volume |
| Others | 67.2 by volume |

The one pass-yield of methacrylic acid based on the fed isobutylene (the total yield including that obtained in the first-stage reaction) was 66.7 mole %.

EXAMPLE 2

The same catalyst as in Example 1 was prepared except that the diameter of the through-hole was changed to 2.0 mm, and the same reaction as in Example 1 was carried. The pressure drop during the reaction and the yield of the product are shown in Table 1.

EXAMPLE 3

The same catalyst as in Example 1 was prepared except that the diameter of the through-hole was changed to 3.0 mm, and the same reaction as in Example 1 was carried out. The pressure drop during the reaction and the yield of the product are shown in Table 1.

COMPARATIVE EXAMPLE 1

Example 1 was repeated except that a catalyst obtained by molding the catalyst of Example 1 into a solid cylindrical shape having an outside diameter of 6.0 mm and a length of 6.6 mm was used. The pressure drop during the reaction and the yield of the product are shown in Table 1.

EXAMPLE 4

1590 grams of ammonium paramolybdate was dissolved in 6000 ml of water. Separately, 87 g of 85% phosphoric acid was diluted with 450 ml of water, and 54 g of copper nitrate and 37 g of arsenic trioxide were dissolved. The resulting solution was added to the aforesaid aqueous solution of ammonium paramolybdate. The mixture was aged by stirring it fully while heating. Separately, 87 g of 85% phosphoric acid was diluted with 450 ml of water, and 69 g of vanadium pentoxide was added. When water was evaporated while stirring it at an elevated temperature, a yellow complex was formed. The complex was added to the reaction precipitate of phosphorus, molybdenum, copper and arsenic, and finally a solution of 42 g of potassium hydroxide in 450 ml of water was added. The solution was concentrated, and the resulting clay-like material was molded into a ring-like shape having an outside diameter of 4.0 mm, a length of 4.4 mm and a through-hole diameter of 1.0 mm. The ring-like molded product was dried at 200° C. for 4 hours, and calcined in air at 400° C. for 5 hours. The catalyst had the following composition in atomic ratio excepting oxygen.

$$Mo_{12}P_2Cu_{0.3}K_1V_1As_{0.5}.$$

Using the resulting catalyst, the same reaction as in Example 1 was carried out except that the reaction temperature was changed to 310° C. The pressure drop during the reaction and the yield of the product are shown in Table 1.

COMPARATIVE EXAMPLE 2

The same reaction as in Example 4 was carried out except that a catalyst obtained by molding the catalyst of Example 4 into a solid cylindrical form having an outside diameter of 4.0 mm and a length of 4.4 mm was used. The pressure drop during the reaction, and the yield of the product are shown in Table 1.

EXAMPLE 5

Ammonium paramolybdate (1696 g) was dissolved in 3400 ml of water, and 184.4 g of 85% phosphoric acid was added to the aqueous solution. Then, a solution of 312 g of cesium nitrate in 1200 ml of water was added, and 194 g of bismuth nitrate and 64.8 of powdery antimony pentoxide were added. Finally, a solution of 40 g of chromic anhydride and 44.4 g of selenium dioxide in 1200 ml of water was added. The mixture was evaporated to dryness by heating. The resulting solid was dried at 130° C. for 16 hours, molded under pressure into a ring-like shape having an outside diameter of 8 mm, a length of 8.8 mm and a through-hole diameter of 3.0 mm, and heat-treated at 450° C. for 2 hours. The catalytic oxide obtained had the following composition in atomic ratio.

$$Mo_{12}P_2Bi_{0.5}Sb_{0.5}Cs_{2.0}Cr_{0.5}Se_{0.5}.$$

The same reaction as in Example 1 was carried out using the resulting catalyst except that the reaction temperature was changed to 340° C. The pressure drop during the reaction and the yield of the product are shown in Table 1.

COMPARATIVE EXAMPLE 3

The same reaction as in Example 5 was carried out except that a catalyst obtained by molding the catalyst of Example 5 into a solid cylindrical shape having an outside diameter of 8.0 mm and a length of 8.8 mm was used. The pressure drop during the reaction and the yield of the product are shown in Table 1.

EXAMPLE 6

Molybdenum trioxide (2000 g), 126.4 g of vanadium pentoxide, 22.1 g of copper oxide, 22.2 g of iron oxide, 20.9 g of tin oxide and 160.2 g of 85% phosphoric acid were dispersed in 20 liters of water. The dispersion was stirred for about 3 hours under heating, and 7.8 g of potassium hydroxide was added to the solution. The mixture was refluxed under boiling for about 3 hours. The aqueous solution was evaporated to dryness. The resulting dry solid was molded into a ring-like shape having an outside diameter of 5.0 mm, a length of 5.5 mm and a through-hole diameter of 2.0 mm, and calcined in air at 350° C. for 2 hours. The resulting catalytic oxide had the following composition in atomic ratio.

$Mo_{10}P_1V_1K_{0.1}Cu_{0.2}Fe_{0.2}Sn_{0.1}$

Using the resulting catalyst, the same reaction as in Example 1 was carried out except that the reaction temperature was changed to 320° C. The pressure drop during the reaction and the yield of the product are shown in Table 1.

COMPARATIVE EXAMPLE 4

The same reaction as in Example 6 was carried out except that a catalyst obtained by molding the catalyst of Example 6 into a solid cylindrical form having an outside diameter of 6 mm and a length of 6.6 mm was used. The pressure drop during the reaction and the yield of the product are shown in Table 1.

EXAMPLE 7

A ring-like catalyst having an outside diameter of 5.0 mm, a length of 5.5 mm and a throughhole diameter of 2.0 mm was prepared in the same way as in Example 1 except that 108.8 g of barium nitrate was used instead of cesium nitrate. The resulting catalytic oxide had the following composition in atomic ratio.

$Mo_{12}P_{1.09}V_{1.09}Ba_{0.5}$

Using the resulting catalyst, the same reaction as in Example 1 was carried out. The pressure drop during the reaction and the yield of the product are shown in Table 1.

COMPARATIVE EXAMPLE 5

The same reaction as in Example 7 was carried out except that a catalyst obtained by molding the catalyst of Example 7 into a solid-cylindrical shape having an outside diameter of 5 mm and a length of 5.5 mm was used. The pressure drop during the reaction and the yield of the product are shown in Table 1.

EXAMPLE 8

Ammonium paramolybdate (1766 g) and 245 g of ammonium paratungstate were dissolved in 8000 ml of heated water. Pyridine (406 g) and 104.8 g of 85% phosphoric acid were added to the solution, and then 1100 g of nitric acid was added. Furthermore, an aqueous solution of 85 g of rubidium hydroxide in 400 ml of water, an aqueous solution of 71 g of zirconium nitrate in 200 ml of water and an aqueous solution of 121 g of cobalt nitrate in 400 ml of water were added. With stirring, the mixture was concentrated by heating. The resulting slurry-like material was molded into a ring-like shape having an outside diameter of 6.0 mm, a length of 6.6 mm and a through hole diameter of 2.0 mm. The catalytic oxide had the following composition in atomic ratio.

$Mo_{12}P_{1.09}W_{1.09}Rb_{1.0}Zr_{0.2}Co_{0.5}$

Using the resulting catalyst, the same reaction as in Example 1 was carried out except that the reaction temperature was changed to 300° C. The results are shown in Table 1.

EXAMPLE 9

Molybdenum trioxide (2000 g), 185 g of niobium pentoxide, 53 g of manganese oxide, 56 g of zinc oxide and 160 g of 85% phosphoric acid were dispersed in 20 liters of water, and with stirring, the dispersion was refluxed for about 3 hours. Strontium nitrate (147 g) was added, and the mixture was further refluxed for about 3 hours. The aqueous solution obtained was concentrated by heating. The resulting dry solid was molded into a ring-like shape having an outside diameter of 6.0 mm, a length of 6.6 mm and a through-hole diameter of 2.0 mm, and calcined in air at 350° C. for 2 hours to form a catalyst having the following composition.

$Mo_{10}P_1Nb_1Sr_{0.5}Mn_{0.5}Zn_{0.5}$

Using the resulting catalyst, the same reaction as in Example 1 was carried out except that the reaction temperature was changed in 320° C. The results are shown in Table 1.

EXAMPLES 10 AND 11

Catalysts having the compositions shown in Table 1 and having a ring-like shape with an outside diameter of 6.0 mm, a length of 6.6 mm and a through-hole diameter of 2.0 mm were prepared in the same way as in Example 1 except that the component D was changed to calcium and magnesium respectively and the components A and B were further added. As raw materials for calcium, magnesium, nickel and silver, their nitrates were used. Germanium oxide was used as a material for germanium, and rhodium chloride was used as a material for rhodium.

The same reaction as in Example 1 was carried out except that each of the catalysts so obtained was used and the reaction temperature was changed to 300° C. The results are shown in Table 1.

COMPARATIVE EXAMPLE 6 TO 9

The same reactions as in Examples 8 to 11 were each carried out except that the catalysts in these examples were each molded into a solid cylindrical shape having an outside diameter of 6 mm and a length of 6.6 mm. The results are shown in Table 1.

TABLE 1

| Example (Ex.) or Comparative Example (CEx.) | Catalyst composition (atomic ratio) | Shape of the catalyst (φ: Outside diameter L: length) | Reaction temperature (°C.) | Conversion of methacrolein (mole %) | Methacrylic acid Selectivity (mole %) | Methacrylic acid One-pass yield (mole %) | Pressure drop (mmHg) |
|---|---|---|---|---|---|---|---|
| Ex. 1 | $Mo_{12}P_{1.09}V_{1.09}Cs_{1.0}$ | 6.0 mmφ × 6.6 mmL (through-hole diameter 1.0 mm) | 290 | 89.3 | 84.6 | 75.5 | 80 |
| Ex. 2 | " | 6.0 mmφ × 6.6 mmL (through-hole diameter 2.0 mm) | 290 | 89.1 | 84.9 | 75.6 | 65 |
| Ex. 3 | " | 6.0 mmφ × 6.6 mmL (through-hole diameter 3.0 mm) | 290 | 89.0 | 85.1 | 75.7 | 60 |
| CEx. 1 | " | 6.0 mmφ × 6.6 mmL | 290 | 89.2 | 83.0 | 74.0 | 90 |
| Ex. 4 | $Mo_{12}P_2Cu_{0.3}K_1V_1As_{0.5}$ | 4.0 mmφ × 4.4 mmL (through-hole diameter 1.0 mm) | 310 | 87.0 | 80.1 | 69.7 | 110 |
| CEx. 2 | " | 4.0 mmφ × 4.4 mmL | 310 | 86.8 | 78.2 | 68.0 | 145 |
| Ex. 5 | $Mo_{12}P_2Bi_{0.5}Sb_{0.5}Cs_{2.0}Cr_{0.5}Se_{0.5}$ | 8.0 mmφ × 8.8 mmL (through-hole diameter 3.0 mm) | 340 | 80.5 | 75.0 | 60.4 | 50 |
| CEx. 3 | " | 8.0 mmφ × 8.8 mmL | 340 | 80.1 | 72.9 | 58.4 | 65 |
| Ex. 6 | $Mo_{10}P_1V_1K_{0.1}Cu_{0.2}Fe_{0.2}Sn_{0.1}$ | 5.0 mmφ × 5.5 mmL (through-hole diameter 2.0 mm) | 320 | 81.8 | 76.2 | 62.3 | 95 |
| CEx. 4 | " | 6.0 mmφ × 6.6 mmL | 320 | 80.9 | 73.9 | 59.8 | 95 |
| Ex. 7 | $Mo_{12}P_{1.09}V_{1.09}Ba_{0.5}$ | 5.0 mmφ × 5.5 mmL (through-hole diameter 2.0 mm) | 290 | 88.5 | 84.2 | 74.5 | 90 |
| CEx. 5 | " | 5.0 mmφ × 5.5 mmL | 290 | 88.1 | 83.0 | 73.1 | 125 |
| Ex. 8 | $Mo_{12}P_{1.09}W_{1.09}Rb_{1.0}Zr_{0.2}Co_{0.5}$ | 6.0 mmφ × 6.6 mmL (through-hole diameter 2.0 mm) | 300 | 89.2 | 83.0 | 74.0 | 65 |
| CEx. 6 | " | 6.0 mmφ × 6.6 mmL | 300 | 88.0 | 81.6 | 71.8 | 90 |
| Ex. 9 | $Mo_{10}P_1Nb_1Sr_{0.5}Mn_{0.5}Zn_{0.5}$ | 6.0 mmφ × 6.6 mmL (through-hole diameter 2 mm) | 320 | 83.7 | 75.1 | 62.9 | 70 |
| CEx. 7 | " | 6.0 mmφ × 6.6 mmL | 320 | 82.0 | 73.6 | 60.4 | 95 |
| Ex. 10 | $Mo_{12}P_{1.09}V_{1.09}Ca_{0.5}Ge_{0.2}Ni_{0.2}$ | 6.0 mmφ × 6.6 mmL (through-hole diameter 2 mm) | 300 | 89.7 | 83.5 | 74.9 | 65 |
| CEx. 8 | " | 6.0 mmφ × 6.6 mmL | 300 | 87.7 | 81.5 | 71.5 | 90 |
| Ex. 11 | $Mo_{12}P_{1.09}V_{1.09}Mg_{0.5}Rh_{0.1}Ag_{0.5}$ | 6.0 mmφ × 6.6 mmL (through-hole diameter 2 mm) | 300 | 88.0 | 83.7 | 73.7 | 65 |
| CEx. 9 | " | 6.0 mmφ × 6.6 mmL | 300 | 86.0 | 82.0 | 70.5 | 90 |

EXAMPLE 12

Ammonium paramolybdate (1766 g) and 106 g of ammonium metavanadate were dissolved in 8000 ml of heated water, and 406 g of pyridine and 105 g of 85% phosphoric acid were added. Then, 1100 g of nitric acid was added, and further a solution of 162 g of cesium nitrate and 40 g of copper nitrate in 1000 ml of water was added, and the mixture was concentrated by heating with stirring. The resulting slurry-like material was dried at 250° C. for 15 hours and pulverized. Then, 34 g of glass fibers having a diameter of 1 to 10 microns and a length of 2 to 4 mm and a small amount of water were added to the pulverized material, and the mixture was molded into a ring-like shape having an outside diameter of 6.0 mm, a length of 6.6 mm and a through-hole diameter of 2.0 mm, dried, and then calcined first in a nitrogen stream at 430° C. for 3 hours and then in air at 400° C. for 3 hours to form a catalyst having the following composition.

$Mo_{12}P_{1.09}V_{1.09}Cs_{1.0}Cu_{0.2}$

Using the resulting catalyst, the same reaction as in Example 1 was continuously carried out for 5000 hours. The results and the variations in the pressure drop of the catalyst layer are shown in Table 2.

COMPARATIVE EXAMPLE 10

The same continuous reaction as in Example 12 was carried out for 5000 hours except that a catalyst obtained by molding the catalyst of Example 12 into a solid cylindrical shape having an outside diameter of 6.0 mm and a length of 6.6 mm was used. The results are shown in Table 2.

EXAMPLE 13

Ammonium paramolybdate (1766 g) and 58 g of ammonium metavanadate were dissolved in 8000 ml of heated water, and 406 g of pyridine and 144 g of 85% phosphoric acid were added. Subsequently, 1100 g of nitric acid was added, and a solution of 40 g of copper nitrate and 118 g of 60% ortho-arsenic acid in 400 ml of water was added, and the mixture was concentrated. The resulting clay-like material was mixed well with 52 g of scale-like graphite having a thickness of 1 to 10 microns and a size of 10 to 50 microns. The mixture was then molded into a ring-like shape having an outside diameter of 5.0 mm, a length of 6.0 mm and a through-hole diameter of 2.0 mm by an extruder, dried, and calcined first in a nitrogen stream at 430° C. for 3 hours and then in air at 400° C. for 3 hours to obtain a catalyst having the following composition.

$$Mo_{12}P_{1.5}V_{0.6}Cu_{0.2}K_{1.0}As_{0.6}$$

The same reaction as in Example 1 was carried out continuously for 3000 hours. The results and the variations in the pressure drop of the catalyst layer are shown in Table 2.

COMPARATIVE EXAMPLE 11

The same continuous reaction as in Example 13 was carried out for 3000 hours except that a catalyst obtained by molding the catalyst of Example 13 into a solid cylindrical shape having an outside diameter of 5.0 mm and a length of 6.0 mm. The results are shown in Table 2.

EXAMPLE 14

A catalyst having the composition $Mo_{12}P_{1.5}V_{0.6}Cs_{1.0}Cu_{0.2}As_{0.6}$ was prepared in the same way as in Example 13 except that 162 g of cesium nitrate was used instead of potassium hydroxide, and the graphite was changed to 34 g of stainless steel scales having a thickness of 1 to 10 microns and a size of 10 to 50 microns.

Using the resulting catalyst, the same continuous reaction as in Example 13 was carried out for 3000 hours. The results shown in Table 2 were obtained.

COMPARATIVE EXAMPLE 12

The same continuous reaction as in Example 14 was carried out for 3000 hours except that a catalyst obtained by molding the catalyst of Example 14 into a solid cylindrical shape having an outside diameter of 5.0 mm and a length of 6.0 mm was used. The results are shown in Table 2.

TABLE 2

| Example (Ex.) or Comparative Example (CEx.) | Catalyst composition (atomic ratio) | Shape of the catalyst (φ: Outside diameter L: length) | Reaction time elapsed (hr) | Reaction temperature (°C.) | Conversion of methacrolein (mole %) | Methacrylic acid Selectivity (mole %) | Methacrylic acid One-pass yield (mole %) | Pressure drop (mmHg) |
|---|---|---|---|---|---|---|---|---|
| Ex. 12 | $Mo_{12}P_{1.09}V_{1.09}Cs_{1.0}Cu_{0.2}$ | 6.0 mmφ × 6.6 mmL (Through-hole diameter 2.0 mm) | 100 | 290 | 90.4 | 85.0 | 76.8 | 65 |
| | | | 5,000 | 300 | 90.1 | 84.8 | 76.4 | 75 |
| CEx. 10 | " | 6.0 mmφ × 6.6 mmL | 100 | 290 | 90.5 | 82.8 | 74.9 | 90 |
| | | | 5,000 | 300 | 86.7 | 80.9 | 70.1 | 120 |
| Ex. 13 | $Mo_{12}P_{1.5}V_{0.6}Cu_{0.2}K_{1.0}As_{0.6}$ | 5.0 mmφ × 6.0 mmL (Through-hole diameter 2.0 mm) | 100 | 290 | 88.3 | 85.1 | 75.1 | 90 |
| | | | 3,000 | 300 | 88.1 | 84.9 | 74.8 | 100 |
| CEx. 11 | " | 5.0 mmφ × 6.0 mmL | 100 | 290 | 88.4 | 82.9 | 73.3 | 125 |
| | | | 3,000 | 300 | 86.0 | 81.4 | 70.0 | 150 |
| Ex. 14 | $Mo_{12}P_{1.5}V_{0.6}Cu_{0.2}Cs_{1.0}As_{0.6}$ | 5.0 mmφ × 6.0 mmL (Through-hole diameter 2.0 mm) | 100 | 285 | 90.5 | 85.3 | 77.2 | 85 |
| | | | 3,000 | 295 | 90.3 | 85.1 | 76.8 | 95 |
| CEx. 12 | " | 5.0 mmφ × 6.0 mmL | 100 | 285 | 90.7 | 83.0 | 75.3 | 120 |
| | | | 3,000 | 295 | 87.7 | 82.0 | 71.9 | 145 |

EXAMPLE 15

The catalyst of Example 2 was used. A gaseous mixture of isobutyric acid, oxygen, steam and nitrogen in a volume ratio of 5.0:10.0:10.0:75.0 was introduced at a space velocity of 2000 hr$^{-1}$ and reacted at a reaction temperature of 280° C. The results are shown in Table 3.

COMPARATIVE EXAMPLE 13

Using the catalyst of Comparative Example 1, the same reaction as in Example 15 was carried out. The results are shown in Table 3.

TABLE 3

| Run | Shape of the catalyst (φ: outside diameter L: length) | Reaction temperature (°C.) | Conversion of isobutyric acid (%) | Methacrylic acid Selectivity (%) | Methacrylic acid One-pass yield (%) | Pressure drop (mmHg) | Maximum temperature of the catalyst layer (°C.) |
|---|---|---|---|---|---|---|---|
| Example 15 | 6.0 mmφ × 6.6 mmL (through-hole diameter 2.0 mm) | 280 | 100 | 79.3 | 79.3 | 155 | 320 |
| Comparative Example 13 | 6.0 mmφ × 6.6 mmL | 280 | 100 | 77.0 | 77.0 | 215 | 332 |

EXAMPLE 16

Using the catalyst of Example 2, a gaseous mixture composed of isobutyraldehyde, oxygen, steam and nitrogen in a volume ratio of 5.0:12.5:10.0:72.5 was introduced at a space velocity of 800 hr$^{-1}$ and reacted at a temperature of 280° C. The results shown in Table 4 were obtained.

COMPARATIVE EXAMPLE 14

Using the catalyst of Comparative Example 1, the same reaction as in Example 16 was carried out. The results are shown in Table 4.

TABLE 4

| Run | Shape of the catalyst (φ: Outside diameter L: length) | Reaction temperature (°C.) | Conversion of isobutyraldehyde (%) | Selectivity (%) Methacrylic acid | Methacrolein | One-pass yield (%) Methacrylic acid | Methacrolein | Pressure drop (mmHg) | Maximum temperature of the catalyst layer |
|---|---|---|---|---|---|---|---|---|---|
| Example 16 | 6.0 mmφ × 6.6 mmL (through-hole diameter 2.0 mm) | 280 | 100 | 67.1 | 14.0 | 67.1 | 14.0 | 35 | 328 |
| Comparative Example 13 | 6.0 mmφ × 6.6 mmL | 280 | 100 | 65.2 | 11.3 | 65.2 | 11.3 | 50 | 345 |

What is claimed is:

1. A catalyst for production of methacrylic acid, said catalyst being molded in a ring-like shape having an outside diameter of 3.0 to 10.0 mm, an inside diameter of 0.1 to 0.7 times the outside diameter and a length of 0.5 to 2.0 times the outside diameter, said catalyst consisting essentially of a catalytically active material having the composition represented by the following general formula $$Mo_aP_bA_cB_dC_eD_fO_x$$

wherein Mo is molybdenum, P is phosphorus, A is at least one element selected from the group consisting of arsenic, antimony, germanium, bismuth, zirconium and selenium, B is at least one element selected from the group consisting of copper, iron, chromium, nickel, manganese, cobalt, tin, silver, zinc and rhodium, C is at least one element selected from the group consisting of vanadium, tungsten and niobium, D is at least one element selected from the group consisting of alkali metals, alkaline earth metals and thallium, and O is oxygen, and a, b, c, d, e, f and x represent the atomic ratios of Mo, P, A, B, C, D and O provided that when a is 12, b is 0.5 to 4, c is 0 to 5, d is 0 to 3, e is 0 to 4 and f is 0.01 to 4 and x is a number determined by the oxidation states of the individual elements.

2. The catalyst of claim 1 which has an outside diameter of 4.0 to 8.0 mm, an inside diameter of 0.2 to 0.6 times the outside diameter and a length 0.7 to 1.3 times the outside diameter.

3. The catalyst of claim 1 wherein the catalytically active material is selected from the group consisting of $Mo_{12}P_{1.09}V_{1.09}Cs_{1.0}$, $Mo_{12}P_2Cu_{0.3}K_1V_1As_{0.5}$, $Mo_{12}P_2Bi_{0.5}Sb_{0.5}Cs_{2.0}Cr_{0.5}Se_{0.5}$, $Mo_{10}P_1V_1K_{0.1}Cu_{0.2}Fe_{0.2}Sn_{0.1}$, $Mo_{12}P_{1.09}V_{1.09}Ba_{0.5}$, $Mo_{12}P_{1.09}W_{1.09}Rb_{1.0}Zr_{0.2}Co_{0.5}$, $Mo_{10}P_1Nb_1Sr_{0.5}Mn_{0.5}Zn_{0.5}$, $Mo_{12}P_{1.09}V_{1.09}Ca_{0.5}Ge_{0.2}Ni_{0.2}$, $Mo_{12}P_{1.09}V_{1.09}Mg_{0.5}Rh_{0.1}Ag_{0.5}$, $Mo_{12}P_{1.09}V_{1.09}Cs_{1.0}Cu_{0.2}$, $Mo_{12}P_{1.5}V_{0.6}Cu_{0.2}K_{1.0}As_{0.6}$, and $Mo_{12}P_{1.5}V_{0.6}Cu_{0.2}Cs_{1.0}As_{0.6}$.

* * * * *